(12) United States Patent
Kurosawa et al.

(10) Patent No.: US 9,316,600 B2
(45) Date of Patent: Apr. 19, 2016

(54) INSPECTION METHOD AND INSPECTION EQUIPMENT FOR MOUTH SECTION OF BOTTLE-CAN

(75) Inventors: Akio Kurosawa, Neyagawa (JP); Tadayuki Sota, Neyagawa (JP); Tadafumi Hirano, Sunto-gun (JP)

(73) Assignees: Kurashiki Boseki Kabushiki Kaisha, Kurashiki-shi (JP); Universal Can Corporation, Tokyo (JP)

( * ) Notice: Subject to any disclaimer, the term of this patent is extended or adjusted under 35 U.S.C. 154(b) by 312 days.

(21) Appl. No.: 14/123,978

(22) PCT Filed: Jun. 4, 2012

(86) PCT No.: PCT/JP2012/064410
§ 371 (c)(1),
(2), (4) Date: Dec. 5, 2013

(87) PCT Pub. No.: WO2012/169471
PCT Pub. Date: Dec. 13, 2012

(65) Prior Publication Data
US 2014/0125796 A1 May 8, 2014

(30) Foreign Application Priority Data
Jun. 6, 2011 (JP) .................................. 2011-126217

(51) Int. Cl.
*H04N 7/18* (2006.01)
*G01N 21/95* (2006.01)
(Continued)

(52) U.S. Cl.
CPC .......... *G01N 21/9515* (2013.01); *B07C 5/3408* (2013.01); *G01N 21/909* (2013.01); *G01N 21/9054* (2013.01)

(58) Field of Classification Search
CPC .......... G01N 21/9054; G01N 21/9515; G01N 21/909; B07C 5/3408
USPC .......................... 348/127, 125, 131, 134, 135
See application file for complete search history.

(56) References Cited

U.S. PATENT DOCUMENTS 4,758,084 A 7/1988 Tokumi et al.
4,915,237 A 4/1990 Chang et al.
(Continued)

FOREIGN PATENT DOCUMENTS

DE 3728183 A1 3/1989
EP 1645340 A1 4/2006
(Continued)

OTHER PUBLICATIONS

Supplementary European Search Report dated Jun. 26, 2015, issued for the corresponding European patent application No. 12796744.6.
(Continued)

*Primary Examiner* — Robert Chevalier
(74) *Attorney, Agent, or Firm* — Locke Lord LLP

(57) ABSTRACT

An inspection method and inspection equipment for mouth section of bottle-can including:
first-inspection process for eliminating the bottle-can in which existence of a low-brightness area is detected from a monochrome inspection-image which is obtained by imaging the curl portion with irradiating white light to the curl portion in an imaging area of the bottle-can which is conveyed along a main-conveyance path; and a second-inspection process for judging quality of the bottle-can while conveying the bottle-can which is eliminated by the first-inspection process along a secondary-conveyance path, by irradiating illumination lights having two colors from different directions to the curl portion in the imaging area along substantially a tangential direction of a cylindrical surface of the mouth section so as to image a color inspection-image, and distinguishing existence or not of the asperity on the curl portion from signal strengths of the light colors of the color inspection-image.

6 Claims, 12 Drawing Sheets

(51) Int. Cl.
*G01N 21/90* (2006.01)
*B07C 5/34* (2006.01)

(56) References Cited

U.S. PATENT DOCUMENTS 6,072,575 A * 6/2000 Loll .................. G01N 21/9054
356/239.1
2009/0107896 A1* 4/2009 Gochar, Jr. ............ B07C 5/3422
209/577

FOREIGN PATENT DOCUMENTS

| JP | 53-120490 A | 10/1978 |
|---|---|---|
| JP | 62-012845 A | 1/1987 |
| JP | 2002-296192 A | 10/2002 |
| JP | 2003-215055 A | 7/2003 |
| JP | 2003-307498 A | 10/2003 |
| JP | 2004-083128 A | 3/2004 |
| JP | 2004-264132 A | 9/2004 |
| JP | 2007-084081 A | 4/2007 |
| JP | 2007-285983 A | 11/2007 |
| JP | 2011-133266 A | 7/2011 |

OTHER PUBLICATIONS

International Search Report dated Sep. 4, 2012, issued for PCT/JP2012/064410.

* cited by examiner

INSPECTION METHOD AND INSPECTION EQUIPMENT FOR MOUTH SECTION OF BOTTLE-CAN

CROSS REFERENCE TO RELATED APPLICATIONS

This application is related to two co-pending applications: "INSPECTION EQUIPMENT FOR SCREW PART OF BOTTLE-CAN" filed even date herewith in the names of Akio Kurosawa and Tadayuki Sota as a national phase entry of PCT/JP2012/064411 and "INSPECTION EQUIPMENT FOR MOUTH SECTION OF BOTTLE-CAN" filed even date herewith in the names of Akio Kurosawa, Tadayuki Sota and Tadafumi Hirano as a national phase entry of PCT/JP2012/064409; which applications are assigned to the assignee of the present application and all incorporated by reference herein.

BACKGROUND OF THE INVENTION

1. Field of the Invention

The present invention relates to inspection method and inspection equipment for mouth section of bottle-can.

Priority is claimed on Japanese Patent Application No. 2011-126217, filed Jun. 6, 2011, the content of which is incorporated herein by reference.

2. Description of the Related Art

A can having a bottle-shape of aluminum alloy in which a cap is screwed on a mouth section having a screw is known as a container filled with contents such as drinks. The can is manufactured by: forming an aluminum alloy sheet into a closed-end cylindrical body which has a bottom plate and a cylindrical side surface in one piece by performing drawing processing and ironing processing (i.e., DI forming); coating an inner surface and an outer surface of the close-ended cylindrical body; forming a shoulder and the mouth section by performing so-called neck-in processing on an opening portion; and performing screw-forming processing, curl-forming processing and the like on the mouth section.

An inner coating in the can is formed by thermo-setting resin such as epoxy-acrylic resin, polyester resin or the like in order to make corrosion resistance and so on to the can with respect to content of the can (refer to Patent Document 1). The inner coating is formed by spraying paint on an inner surface of the can after the drawing and ironing processing before the neck-in processing. However, the paint may scatter around or may cleave to the outer surface of the can and tiny protrusions are formed, so that the protrusions may preface with corrugations when the neck-in processing is performed.

A curl portion is formed by folding an upper end of the mouth section outward and the inner coating is formed an outer surface of the curl portion. The can is hermetically sealed by attaching a cap so as to press a liner to the curl portion (refer to Patent Document 2). Therefore, if asperity such as the aforementioned corrugations by the paint is formed on the surface of the curl portion, especially on a top surface, or deformation such as a pit is formed on the curl portion, the content may be leaked. However, there is a case in which the asperity is formed on the surface of the curl portion by the inner coating being crumpled when the mouth section and the curl portion are formed.

Therefore, it is important that the curl portion is not deformed and the asperity such as the corrugations and the like are not formed on the top surface of the curl portion. Furthermore, in case of the asperity is formed, it is expected that the asperity is detected in an inspection process and reliably excluded as a defective.

For example, as a detection method for detecting fine asperity (e.g., corrugation or the like) formed on the outer surface, a detection method in which a can-body is irradiated obliquely to a tangent plane (i.e., a plane along a tangent line of the outer surface) so that corrugations are detected by observing reflection or shade of the corrugations along the tangent plane is suggested (refer to Patent Document 3).

PRIOR ART DOCUMENT

Patent Document

[Patent Document 1] Japanese Unexamined Patent Application, First Publication No. 2007-84081
[Patent Document 2] Japanese Unexamined Patent Application, First Publication No. 2004-83128
[Patent Document 3] Japanese Unexamined Patent Application, First Publication No. 2004-264132

SUMMARY OF THE INVENTION

Problems to be Solved by the Invention

In the bottle-can, the asperity on the curl portion should be reliably detected since it causes liquid leakage. On the other hand, since color figure without asperity such as punch-figure or blot by DI forming do not affect sealing performance, it is not necessary to exclude a bottle-can having such the color figure. If the color figure is detected as the asperity, non-defective may be excluded as a defective product, so that yield may be deteriorated.

In the inspection method described in Patent Document 3, since the corrugations are detected by checking shade by illumination light for the can, there is a bare possibility that the color figure is detected as defective by this method. However, since it is necessary to position the can with respect to the illumination light and a camera, a correct detection result may be hard to be obtained if the can is receded from a detection position.

In this sort of inspection equipment, processing time is long for individual inspections, so that productivity is deteriorated. If imaging device is added and a plurality of inspection device are provided, even though it is possible to shorten the processing time by inspecting a plurality of cans at the same time, there is a problem that a cost for constructing the inspection equipment is increased.

The present invention is achieved in consideration of the above circumstances, and has an object to provide inspection method and inspection equipment for mouth section of bottle-can which can reliably detect only a bottle-can having asperity such as a flaw or the like which may cause liquid leakage or the like, and which can shorten the processing time for inspection with excellent productivity.

Means for Solving the Problem

An inspection method for a mouth section of a bottle-can according to the present invention, with respect to the bottle-can having the cylindrical mouth section in which a curl portion is fainted by curling an open end thereof for a cap with a liner to be put on, by taking an image of an imaging area which is set to include a part of the curl portion for detecting asperity at the curl portion while rotating the bottle-can around a can-axis, the inspection method has steps of: a first-inspection process the eliminating the bottle-can in which existence of a low-brightness area is detected from a monochrome inspection-image which is obtained by imaging the curl portion with irradiating white light to the curl portion in an imaging area of the bottle-can which is conveyed along a main-conveyance path continuously and sequentially; and a second-inspection process for judging quality of the bottle-can while conveying the bottle-can which is eliminated by the first-inspection process along a secondary-conveyance path deviated from the main-conveyance path, by irradiating illumination lights having two colors from different directions to the curl portion in the imaging area along substantially a tangential direction of a cylindrical surface of the mouth section so as to image a color inspection-image, and distinguishing existence or not of the asperity on the curl portion from signal strengths of the light colors of the color inspection-image.

A part including a roll-figure, a punch-figure, a blot or the like has a color different from the other part and becomes the low-brightness area since reflected-light quantity of the white light irradiated from a white-light source changes. In the first-inspection process, by irradiating the white light to the curl portion in the imaging area, not only asperity such as a flaw but a two-dimensional blot or the like without asperity is detected as a low-brightness area. Therefore, by eliminating the bottle-can in which the low-brightness area detected in spite of whether or not having the asperity the bottle-can having no blot or asperity can be picked out instantly. Those bottle-cans without the blot or the asperity are conveyed along the main-conveyance path; and only the bottle-can eliminated at the first-inspection process is sent to the second-conveyance path and secondary-inspected.

In the secondary-inspection process, by judging the color inspection-image, it is possible to inspect more densely. In the secondary-inspection process, by irradiating the illumination lights having two colors from the different directions to the curl portion of the imaging area, the reflected lights at the asperity which is formed so as to obstruct the illumination lights is captured as a stripe of two colors depending on the light colors of the illumination lights. On the other hand, the reflected light by the blot or the like without the asperity does not make a stripe but is captured as a light and shade by mixed colors of the illumination lights. Therefore: the asperity which may cause liquid leakage can be reliably detected; the blot or the like is not mistaken for the asperity; and it is possible to pick out only the bottle-can having the two-dimensional blot or the like which does not deteriorate a sealing performance between the mouth section and the cap of the bottle-can. As a result, it is possible to reliably eliminate only the bottle-can having the asperity such as a flaw or the like.

As explained above, while inspecting by the white light in the first-inspection process at high speed, the bottle-cans in which the low-brightness area is detected in spite of whether or not having the asperity are all eliminated, and then only those bottle-cans are inspected by the color inspection-image in the secondary-inspection process with accuracy. Accordingly, the bottle-can having the asperity such as the flaw can be reliably eliminated, and it is possible to shorten the processing time of the inspection.

In the inspection method for mouth section of bottle-can according to the present invention, it is preferable that in the second-inspection process, third illumination light having a light color different from that of the illumination lights having two colors be irradiated to a part to which the illumination lights having two colors are irradiated at the curl portion from a cross direction to the illumination lights having two colors.

It is possible to detect an edge position of the curl portion by reflected light of the third-illumination light, so that the curl portion in the color inspection-image can be specified based on the edge position. Accordingly; the figure of the curl portion is defined, and a dimple or distortion of the curl portion can be detected. If the can-axis is deviated from the rotating shaft of the rotating device when rotating the bottle-can, the curl portion moves in the inspection image. However, it is possible to specify the curl portion by detecting the edge position of the curl portion, so that the curl portion can be reliably inspected.

Inspection equipment for a mouth section of a bottle-can according to the present invention, with respect to the bottle-can having the cylindrical mouth section in which a curl portion is formed by curling an open end thereof for a cap with a liner to be put on, by taking an image of an imaging area which is set to include a part of the curl portion for detecting asperity at the curl portion while rotating the bottle-can around a can-axis, the inspection equipment is provided with a main-conveyance path which conveys a bottle-can sequentially; a first-inspection device which eliminates the bottle-can in which existence of a low-brightness area is detected from a monochrome inspection-image which is obtained by imaging the curl portion with irradiating white light to the curl portion in an imaging area of the bottle-can which is conveyed along the main-conveyance path continuously and sequentially; a secondary-conveyance path which conveys the bottle-can which is eliminated by the first-inspection device; and a second-inspection device which judges quality of the bottle-can while conveying the bottle-can along a secondary-conveyance path, by irradiating illumination lights having two colors from different directions to the curl portion in the imaging area so as to image a color inspection-image, and distinguishing existence or not of the asperity on the curl portion from signal strengths of the light colors of the color inspection-image.

In the inspection equipment for mouth section of bottle-can, the first-inspection device is provided with: a first-rotating device which holds the bottle-can and rotates the bottle-can around the can-axis; a white-light illumination device which irradiates white light to the curl portion in the imaging area; a first-imaging device which images the imaging area in monochrome; and a first-judging device which eliminates the bottle-can based on a detection result of detecting the low-brightness area from the monochrome inspection-image obtained by the first-imaging device, and the second-inspection device is provided with: a second-rotating device which holds the bottle-can which is eliminated by the first-inspection device and rotates the bottle-can around the can-axis; a first-illumination device which irradiates a first-illumination light to the curl portion in the imaging area of the bottle-can along substantially a tangential direction of a cylindrical surface of the mouth section; a second-illumination device which irradiates a second-illumination light having a light color different from that of the first-illumination device to a part to which the first-illumination light is irradiated at the curl portion from an opposite side of the first-illumination light with the imaging area in between along substantially the tangential direction of the mouth section; a second-imaging device which images the imaging area in color; and a second-judging device which judges quality of the bottle-can by distinguishing the existence or not of the asperity from the signal strengths of the light colors of the color inspection-image obtained by the second-imaging device.

In the inspection equipment for mouth section of bottle-can according to the present invention, it is preferable that the second-inspection device further include a third-illumination device which irradiates third illumination light having a light color different from that of the illumination lights having two colors to a part to which the illumination lights having two colors are irradiated at the curl portion from across direction to the illumination lights having two colors.

Effects of the Invention

According to the present invention, it is possible to eliminate a bottle-can having asperity such as a flaw or the like, to shorten a processing time of inspection, and to improve productivity.

DETAILED DESCRIPTION OF THE INVENTION

Below embodiment of inspection equipment and an inspection method for mouth section of bottle-can according to the present invention will be explained.

Figure 1:
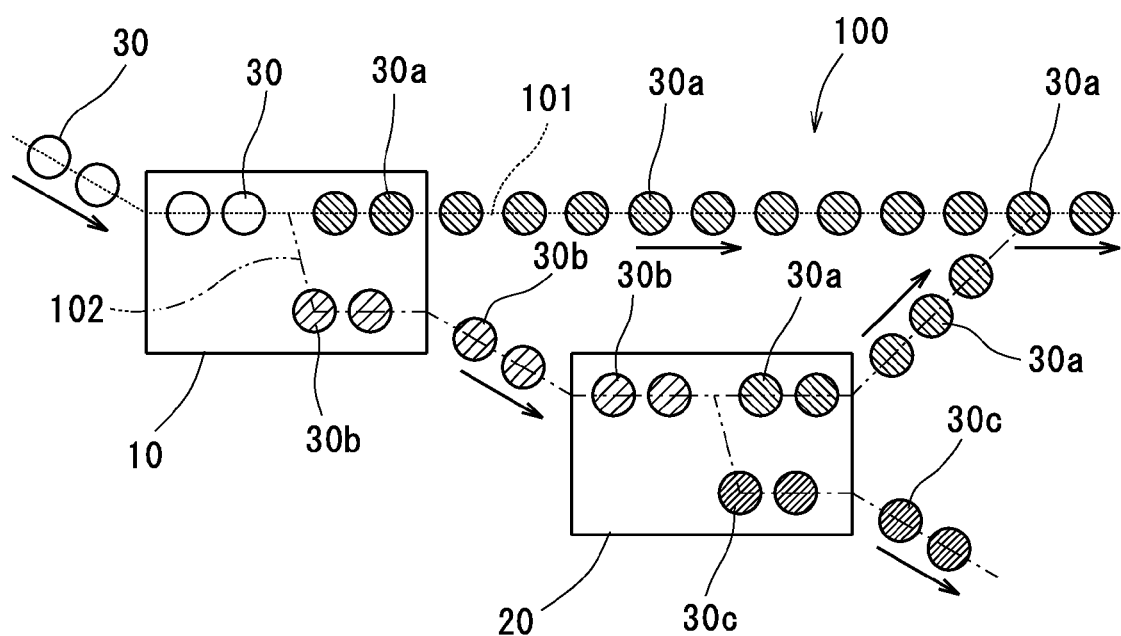
FIG. 1 It is a schematic view showing inspection equipment for mouth section of bottle-can according to the present invention.
Figure 2:
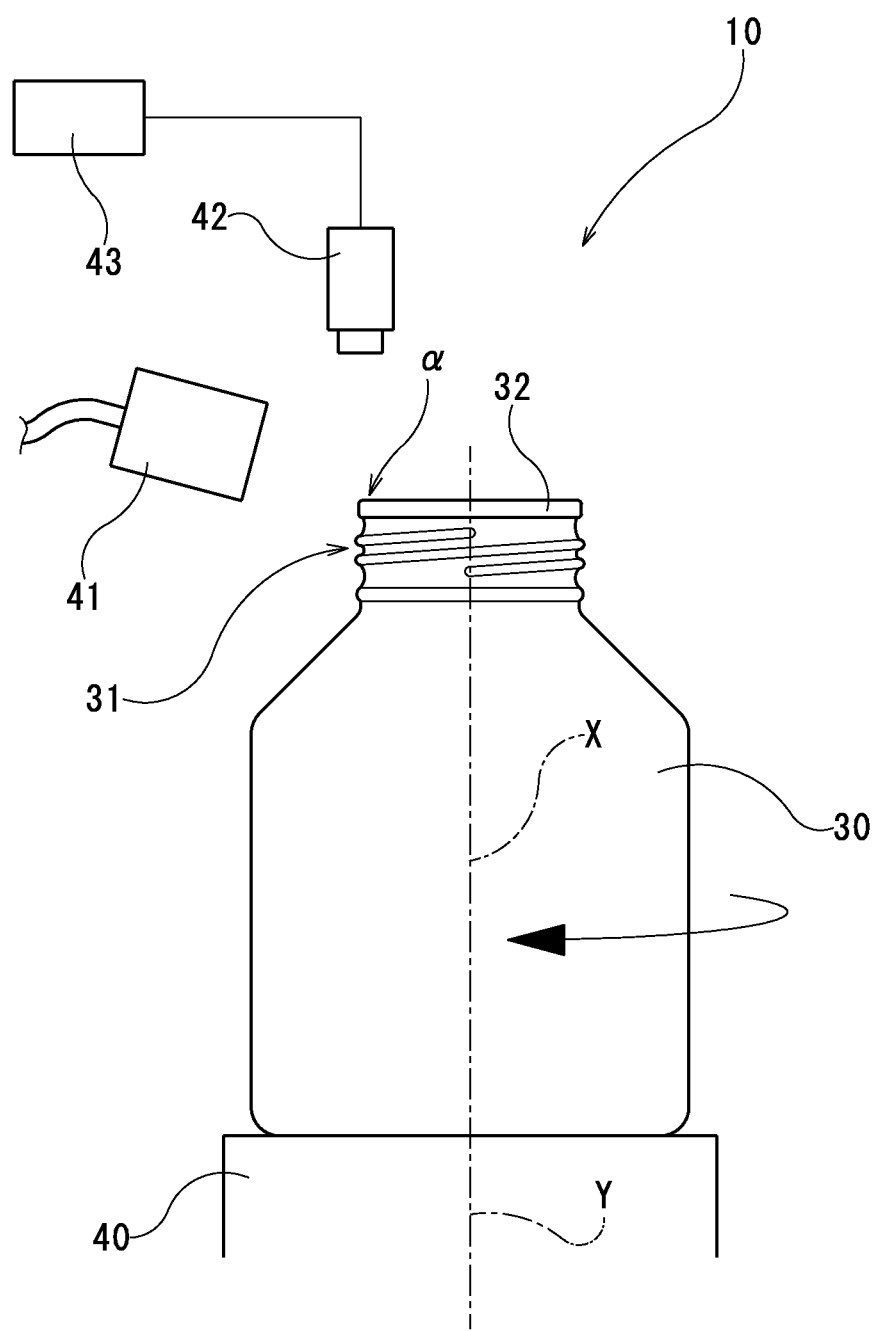
FIG. 2 It is a side view showing a first-inspection device.
Figure 3:
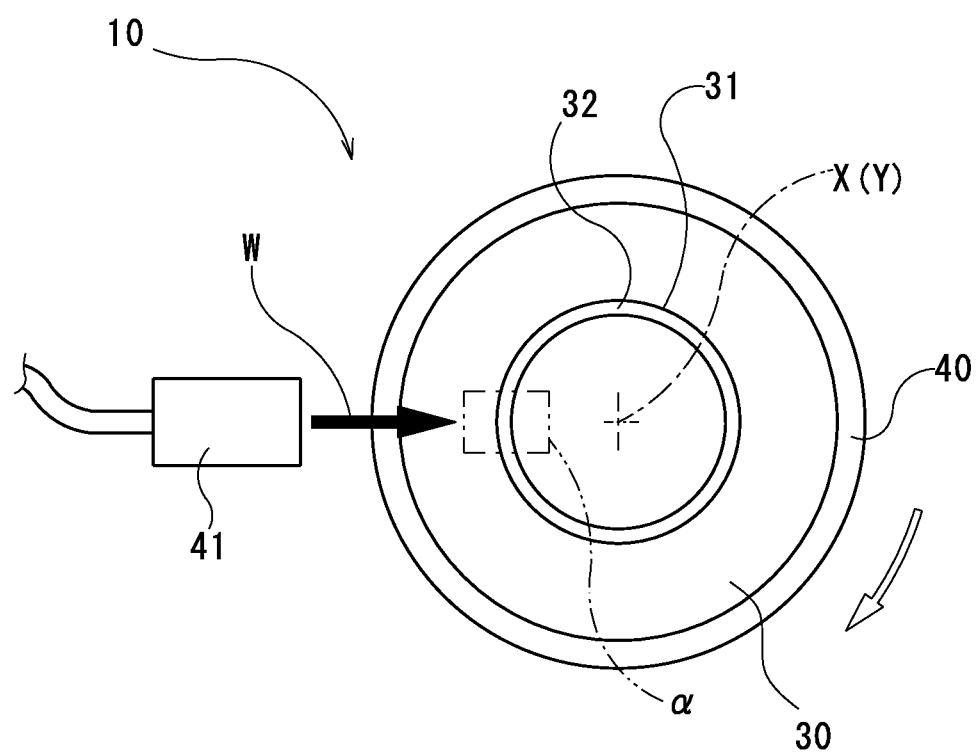
FIG. 3 It is a top view showing the first-inspection device shown in FIG. 2.

Inspection equipment 100 for mouth section shown in FIG. 1 (hereinafter, "inspection equipment") is equipment, with respect to a bottle-can 30 having a cylindrical mouth section 31 in which a curl portion 32 is formed by curling an open end thereof outward for a cap with a liner (not illustrated) to be put on as shown in FIG. 2, for detecting asperity at the curl portion 32 in an imaging area α which is set to include a part of the curl portion 32 (i.e., a part of a top surface in this embodiment) as shown in FIG. 3.

The bottle-can 30 which is inspected in the inspection equipment 100 is, as shown in FIG. 1, conveyed in single-row by a main-conveyance path 101 such as a conveyer or the like in a manufacturing line. In a middle of the main-conveyance path 101, the inspection equipment 100 is provided to inspect the mouth section 31 while rotating the bottle-can 30.

As shown in FIG. 1, the inspection equipment 100 includes two inspection devices of: a first-inspection device 10 which eliminates the bottle-can 30b in which existence of a low-brightness area is detected from a monochrome inspection-image which is obtained by imaging the curl portion 32 with irradiating white light W to the curl portion 32 in the imaging area α of the bottle-can 30 which is conveyed along the main-conveyance path 101 continuously and sequentially; and a second-inspection device 20 which judges quality of the bottle-can 30b eliminated by the first-inspection device 10 while conveying the bottle-can 30b sequentially along a secondary-conveyance path 102 which is deviated from the main-conveyance path 101, by irradiating illumination lights having two colors from different directions to the curl portion 32 in the imaging area α of the bottle-can 30b so as to image a color inspection-image, and distinguishing existence or not of the asperity from signal strengths of the light colors of the color inspection-image.

As shown in FIG. 2 and FIG. 3, the first-inspection device 10 is provided with: a first-rotating device 40 which holds the bottle-can 30 and rotates the bottle-can 30 around a can-axis X; a white-light illumination device 41 which irradiates white light W to the curl portion 32 in the imaging area α; a first-imaging device 42 which images the imaging area α in monochrome; and a first-judging device 43 which eliminates the bottle-can by detecting the low-brightness area from the monochrome image obtained by the first-imaging device 42.

As shown in FIG. 2, the white-light illumination device 41 is disposed so as to irradiate toward the mouth section 31 in the imaging area α (i.e., a part of a top surface of the curl portion 32) from diagonally above. The first-imaging device 42 is disposed above the mouth section 31 of the bottle-can 30 toward the imaging area α (i.e., toward the top surface of the curl portion 32).

Figure 4:
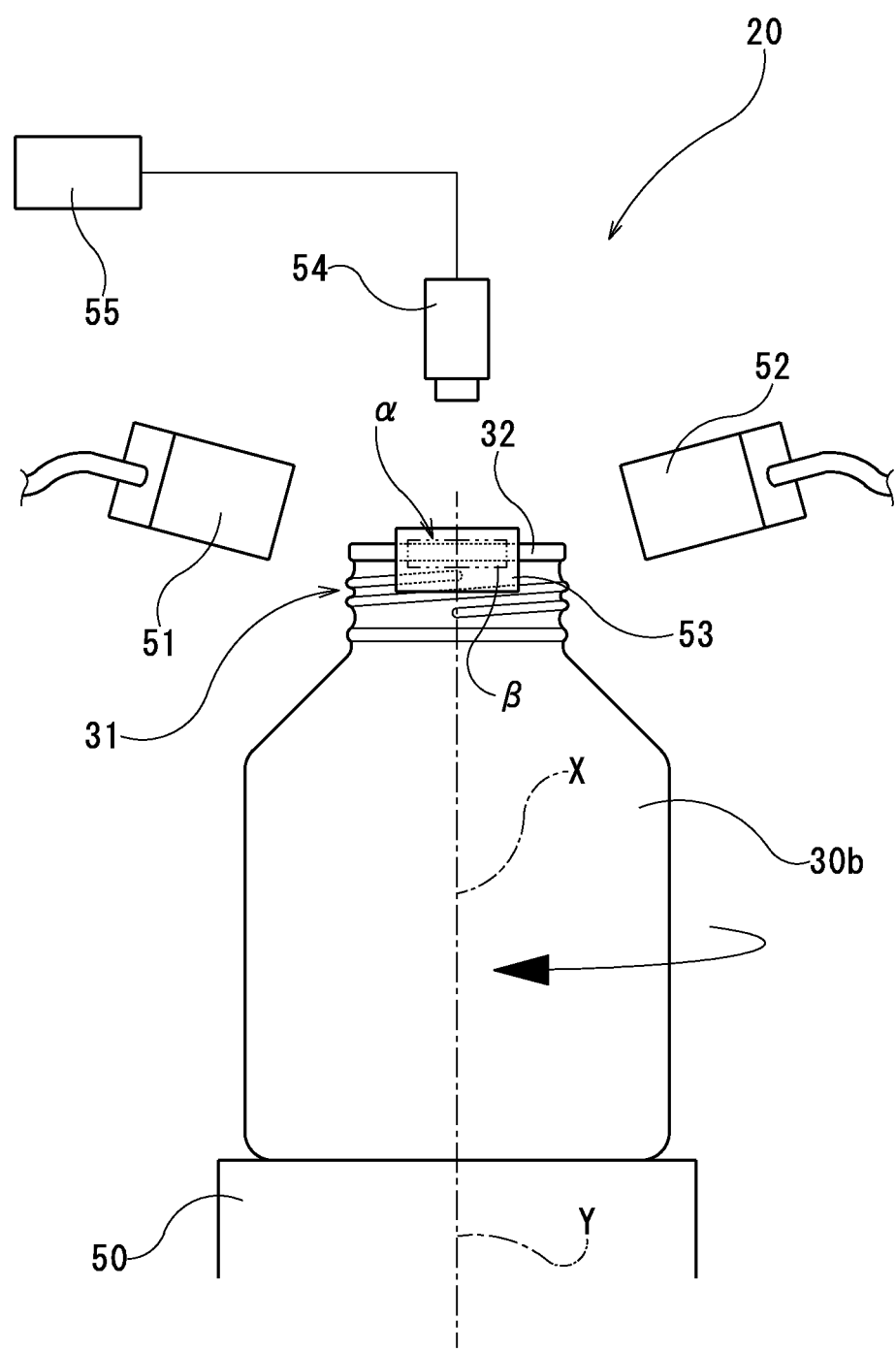
FIG. 4 It is a side view showing a second-inspection device.
Figure 5:
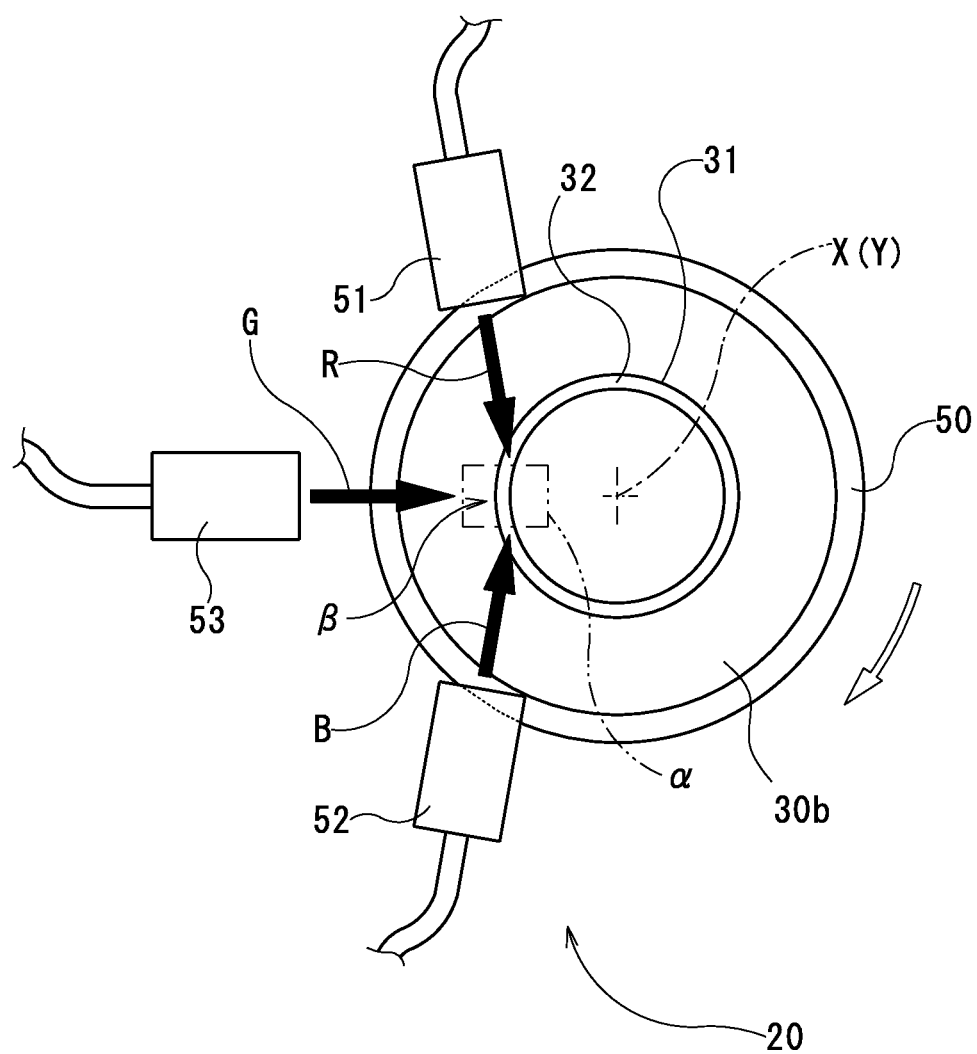
FIG. 5 It is a top view showing the second-inspection device shown in FIG. 4.

As shown in FIG. 4 and FIG. 5, the second-inspection device 20 is provided with: a second-rotating device 50 which holds the bottle-can 30b which is eliminated by the first-inspection device 10 and rotates the bottle-can 30b around the can-axis; a first-illumination device 51 which irradiates a red first-illumination light R to the curl portion 32 in the imaging area α; a second-illumination device 52 which irradiates a blue second-illumination light B to the curl portion 32 in the imaging area α; a third-illumination device 53 which irradiates a green third-illumination light G to a part to which the first-illumination light R and the second-illumination light B are irradiated at the curl portion 32; a second-imaging device 54 which obtains a color inspection-image including reflected lights at the curl portion 32; and a second-judging device 55 which judges quality of the bottle-can 30b based on the color inspection-image obtained by the second-imaging device 54.

The first-illumination device 51 and the second-illumination device 52 are disposed so as to irradiate the first-illumination light R and the second-illumination light B to the mouth section 31 in the imaging area α (i.e., a part of the top surface of the curl portion 32) (shown in FIG. 5). The third-illumination device 53 is disposed so as to irradiate the third-illumination light G to an outer circumferential surface (i.e., an edge-detection area β) which is bent and extended from the part to which the first-illumination light R and the second illumination light B are irradiated in the curl portion 32.

As shown in FIG. 4 and FIG. 5, the first-illumination device 51 is disposed at a side of the mouth section 31 of the bottle-can 30b and irradiates the red first-illumination light R to the top surface of the curl portion 32 in the imaging area α along substantially a tangential direction of a cylindrical surface of the mouth section 31.

As shown in FIG. 4 and FIG. 5, the second-illumination device 52 is disposed at an opposite side of the first-illumination device 51 with the imaging area α in between and irradiates the blue (i.e., a light color different from the red first-illumination light R) second-illumination light B to the part to which the first-illumination light R is irradiated in the curl portion 32 along substantially the tangential direction of the cylindrical surface of the mouth section 31.

That is to say, to the curl portion 32 in the imaging area α, as shown in FIG. 5, by the first-illumination device 51 and the second-illumination device 52, the first-illumination light R and the second-illumination light B are irradiated from the different directions in a state of being overlapped.

In the bottle-can 30b, the edge-detection area β is bent and extended from the imaging area α, and is set so as to include an outer circumferential surface of the curl portion 32. As shown in FIG. 4 and FIG. 5, the third-illumination device 53 is disposed at the side of the mouth section 31 of the bottle-can 30b, and irradiates the green (i.e., a light color different from the first-illumination light R and the second-illumination light B) third-illumination light G to the outer circumferential surface of the curl portion 32 in the edge-detection area β from a cross direction to the first-illumination light R and the second-illumination light B, i.e., along substantially orthogonal direction to the tangential direction of the cylindrical surface of the mouth section 31.

As shown in FIG. 4, the second-imaging device 54 is disposed above the mouth section 31 of the bottle-can 30b toward the imaging area α (i.e., toward the top surface of the curl portion 32), and can image the color inspection-image including the reflected lights at the curl portion 32.

Next, an inspection method for mouth section of bottle-can using the inspection equipment 100 configured above ill be explained.

The bottle-can 30 is conveyed in single-row by the main-conveyance path 101 of a conveyer or the like in a manufacturing line, and is inspected by the inspection equipment 100 which inspects the mouth section 31 while rotating the bottle-can 30 at the middle of the main-conveyance path 101.

First Inspection Process

The bottle-cans 30 are conveyed along the main-conveyance path 101 to the first-inspection device 10 continuously, and are first-inspect. In the first-inspection device 10, by rotating the bottle-can 30 around the can-axis X by the first-rotation device 40 with respect to the white-light nation device 41 and the first-imaging device 42, the whole circumferential of the mouth section 31 is inspected, and a monochrome inspection-image in the imaging area α is captured. The monochrome inspection-image is inputted to the first-judging device 43 which is connected to the first-imaging device 42.

The first-judging device 43 which is connected to the first-imaging device 42 captures the monochrome inspection-image which is obtained by the first-imaging device 42, detects existence of the low-brightness area from the monochrome inspection-image, and eliminates the bottle-can 30b in which the low-brightness area is detected.

A part including a roll-figure, a punch-figure, a blot or the like has a color different from the other part and is captured as the low-brightness area since the reflected-light quantity of the white light \V irradiated from the white-light illumination device 41 is changed. The bottle-can 30b is eliminated if the low-brightness area which is larger than a prescribed size is detected in the monochrome inspection-image.

In the first-inspection process, not only asperity such as a flaw but also a two-dimensional blot or the like without asperity is detected as a low-brightness area. The bottle-can in which the low-brightness area is detected is eliminated in spite of whether or not having the asperity, so that a bottle-can 30a having no blot or asperity can be picked out instantly. The bottle-can 30a having no blot or asperity is conveyed along the main-conveyance path 101. Only the bottle-can 30b in which the low-brightness area is detected is sent to the second-conveyance path 102 and secondary-inspected.

Second-Inspection Process

In the second-conveyance path 102, conveyance speed is set slower than that in the main-conveyance path 101, so that the bottle-can 30b which is eliminated at the first-inspection device 10 is strictly inspected in the second-inspection device 20. In the second-inspection device 20, with respect to the illumination devices 51 to 53 and the second-imaging device 54, by rotating the bottle-can 30b around the can-axis X by the second-rotating device 50, the whole circumference of the mouth section 31 is scanned, and a color inspection-image including the reflected lights at the curl portion 32 is captured. The color inspection-image is inputted to the second-judging device 55 which is connected to the second-imaging device 54, and used for quality determination of the bottle-can 30b.

The second-judging device 55 which is connected to the second-imaging device 54 captures the color inspection-image obtained by the second-imaging device 54, and judges the quality of the bottle-can 30b based on the color inspection-image.

In the color inspection-image of an area including asperity, as described below, the reflected lights at the asperity are captured as a stripe of two colors depending on the light colors of the illumination lights. On the other hand, the reflected lights at an area without asperity such as a blot does not make a stripe but are captured as a light and shade by mixed colors of the illumination lights. Accordingly, the second-judging device 55 judges the bottle-can to be "bad" if the asperity which may cause liquid leakage is detected from the color inspection-image, or judges the bottle-can to be "good" if the bottle-can has only the two-dimensional blot or the like and does not matter of the liquid leakage or the like. Then, the bottle-can 30c which is judged to be "bad" is eliminated from the manufacturing line along the second-conveyance path 102; and the bottle-can 30a which is judged to be "good" is sent back to the main-conveyance path 101.

Figure 6:
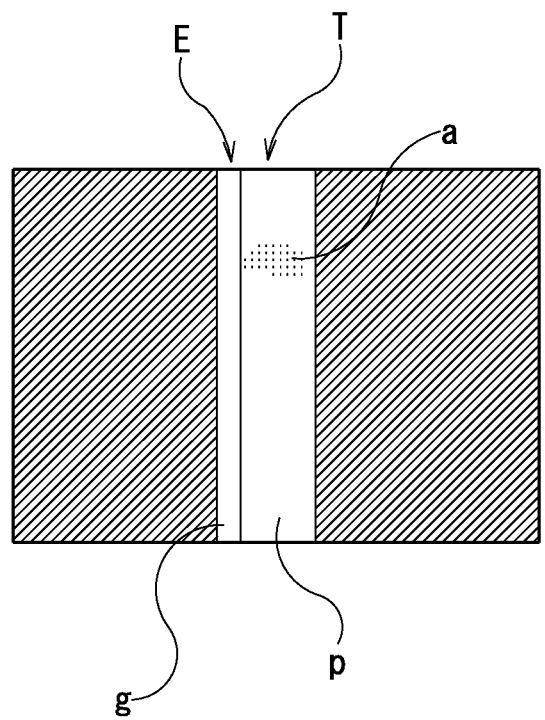
FIG. 6 It is a view showing an inspection image in which a curl portion without asperity is captured in the inspection equipment shown in FIG. 1.

Recognition of asperity will be specifically explained. If the curl portion 32 has no asperity and is flat, at a top surface T in an inspection image, equable purple reflected light "p" which is mixed color of the first-illumination light R and the second-illumination light B is captured (FIG. 6). At a part "a" of color-figure such as flat roll-figure, punch-figure, a blot or the like, shade of the purple of the reflected light "p" is changed.

Figure 7:
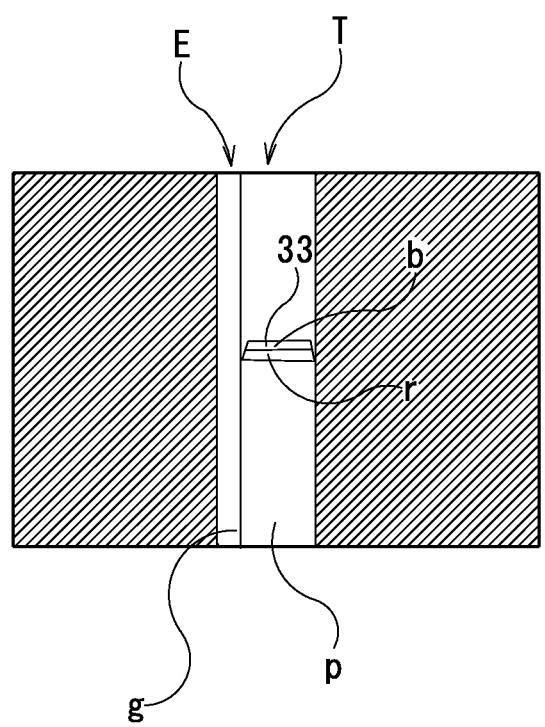
FIG. 7 It is a view showing an inspection image in which a curl portion with asperity formed on a top surface thereof is captured in the inspection equipment shown in FIG. 1.

On the other hand, if asperity which changes reflection directions of the illumination lights is formed on the curl portion 32 (e.g., a dimple 33), the first-illumination light R and the second-illumination light B do not reflected in the same way since irradiated from different directions, so that a red reflected light "r" or a blue reflected light "b" is generated depending on a shape of the dimple 33 as shown in FIG. 7. It can be recognized that the asperity such as the dimple 33 is formed on the curl portion 32 by detecting the reflected light "r" or "b" by the second-judging device 55.

The irradiation directions of the first-illumination light R and the second-illumination light B are along substantially the tangential direction of the cylindrical surface of the mouth section 31, so that the dimple 33 which extends along the radial direction of the bottle-can 30b can be easily detected on the curl portion 32.

As shown in FIG. 6, in the color inspection-image obtained by the second-imaging device 54, reflected light "g" of the third-illumination light G at the edge-detection area β is detected. The second-judging device 55 detects an edge position of the imaging area α from the reflected light "g", and specifies the imaging area α in the color inspection-image based on the edge position.

More specifically, by a computer (not illustrated) which captures the color inspection-image, tracking the image of the reflected light "g" of the third-illumination light and setting the image as an edge of the curl portion 32, so that an area of a prescribed width from the edge is deduced as the imaging area α. Then, the images of the reflected light "r" of the first-illumination light R and the reflected light "b" of the second-illumination light B in the imaging area α are recognized, and from the result, asperity is identified. Furthermore, if displacement of the image of the reflected light "g" of the third-illumination light G exceeds a prescribed value of radial displacement of the curl portion 32, it is distinguished as defect of the edge.

Figure 8:
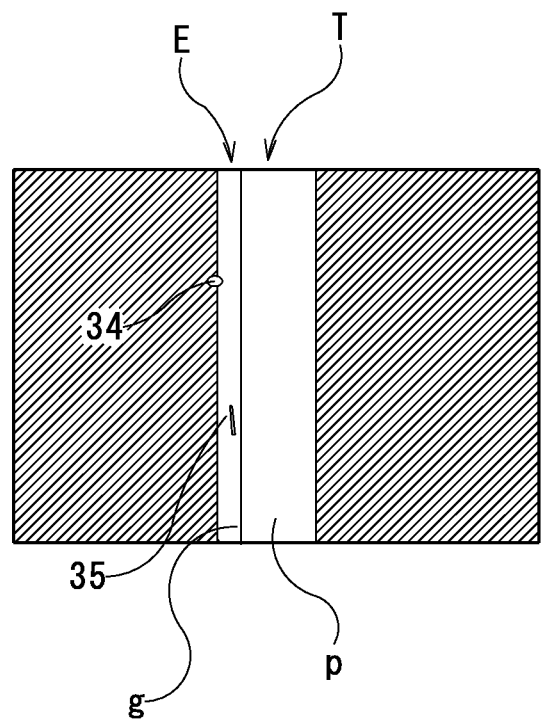
FIG. 8 It is a view showing an inspection image in which a curl portion with a dent or a flaw is captured in the inspection equipment shown in FIG. 1.

In a case in which asperity such as a pit 34 or the like is formed on the edge of the curl portion 32, as shown in FIG. 8, the reflected light "g" is generated to have a figure according to a figure of the pit 34. Therefore, by detecting the reflected light "g" having such the figure, it is possible to detect the pit 34 or the like formed on the edge of the curl portion 32.

Figure 9:
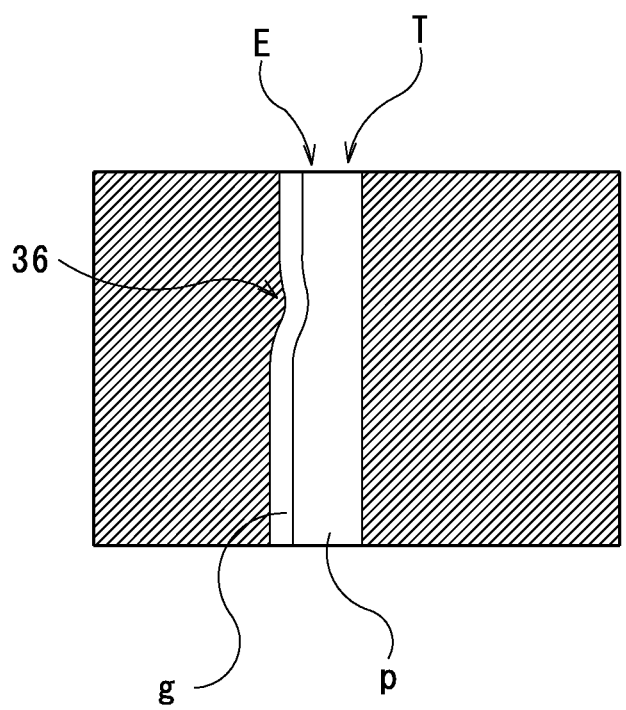
FIG. 9 It is a view showing an inspection image in which a curl portion with a bend part formed on an outer circumferential surface is captured in the inspection equipment shown in FIG. 1.

Since the asperity such as the flaw 35 or the like formed on the edge of the curl portion 32 makes diffusion of the third-illumination light G, by detecting the diffusion, it is possible to detect the flaw 35 on the outer circumferential surface of the curl portion 32. In a case in which a local bent part 36 is formed as shown in FIG. 9, since the reflected light "g" shows a bent figure according to the figure in the edge-detection area β, it is possible to detect the bent part 36 on the curl portion 32 by detecting such the figure.

Moreover, in the inspection devices of the inspection equipment 100, by rotating the bottle-can 30 by the rotating devices 40 and 50, the whole circumstance of the mouth section 31 can be scanned.

Figure 10:
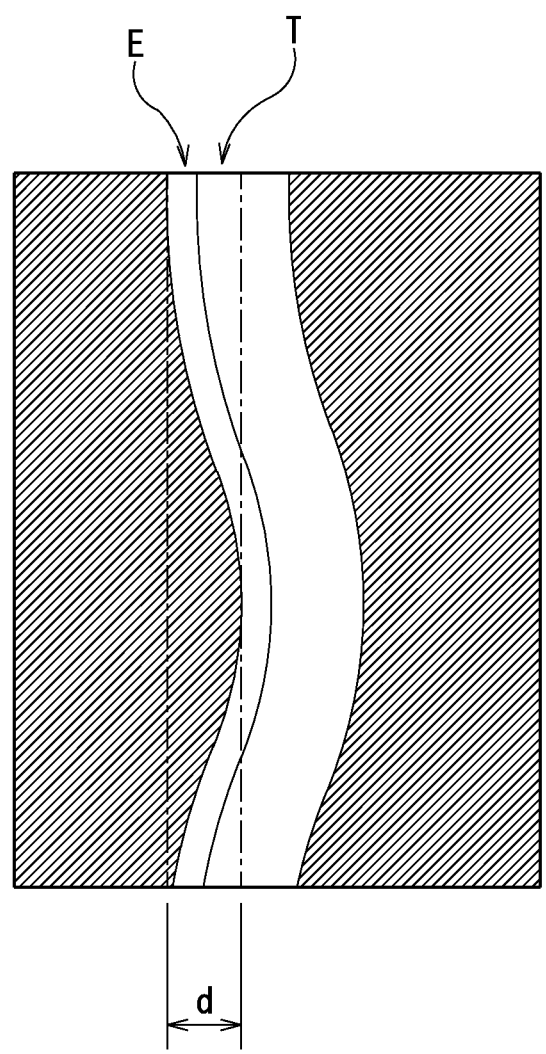
FIG. 10 It is a view showing an inspection image which is obtained by imaging a curl portion while rotating the bottle-can which is deviated from a rotating axis in the inspection equipment shown in FIG. 1.

In the second-inspection process, if the can-axis X of the bottle-can 30b is deviated from a rotating axis Y of the second-rotating device 50, as shown in FIG. 10, the position of the curl portion 32 in the color inspection-image captured by the second-imaging device 54 is largely meandered along with the rotation of the bottle-can 30b, it is difficult to detect a defect such as the bent or the like of the curl portion 32. However, in the second-inspection device 20, since the green reflected light "g" from the edge-detection area β indicates an edge position E of the curl portion 32, by tracking the reflected light "g" (i.e., the edge position E), it is possible to inspect while specifying the curl portion 32. Furthermore, by detecting a local deformation 37 of the green reflected light "g", it is possible to detect a defect such as the bent deformation or the like of the curl portion 32.

Figure 11:
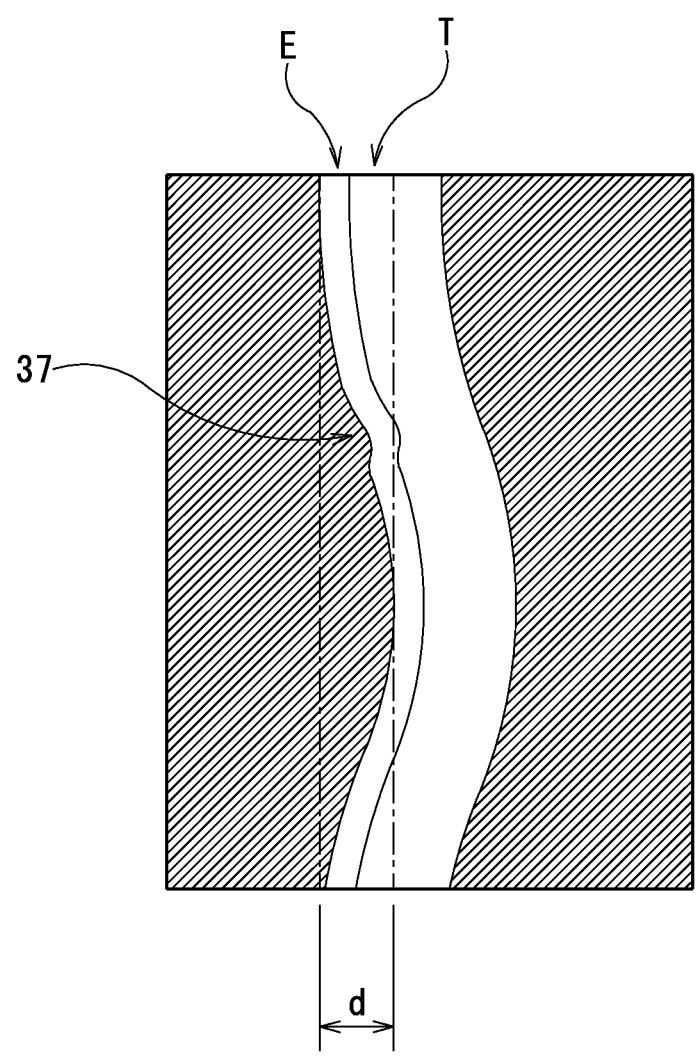
FIG. 11 It is a view showing an inspection image which is obtained by imaging a curl portion while rotating the bottle-can which is deviated from a rotating axis in the inspection equipment shown in FIG. 1, in a state in which a dent is formed on an outer circumferential surface of the curl portion.

FIG. 10 and FIG. 11 show color inspection-images of the mouth section 31 which are obtained by imaging the bottle-can 30b while rotating in the second-inspection process. In the color inspection-images, in a case in which the can-axis X of the bottle-can 30b is deviated from the rotating axis Y of the second-rotating device 50 at a distance "d", the edge position E is gently meandered at a width "d" as an eccentricity (FIG. 10). On the other hand, in a case in which the mouth section 31 is deformed, as shown in FIG. 11, a local deformation 37 having a form clearly different from the bent form of the whole edge position E is generated. Accordingly, since the bent part of the curl portion 32 can be easily detected by the detection of the deformation 37, a defect can be reliably detected while properly recognizing the curl portion 32 even though the bottle-can 30b is eccentrically rotated.

It will be explained to detect asperity in the color inspection-image referring to FIG. 12. In a case in which the surface of the curl portion 32 is flat, the reflected light "r" of the red first-illumination light R and the reflected light "b" of the blue second-illumination light B are mixed and enter the second-imaging device 54, no that the purple reflected light "p" is detected. With respect to a part in which color-figure such as a blot adhered to the curl portion 32, roll-figure or the like is generated without asperity, roll-figure or the like, the purple reflected light "p" is detected since the first-illumination light R and the second-illumination light B are reflected. However, in a case in which asperity such as the dimple 33 or the like which prevents the illumination lights R and B from entering is formed on the curl portion 32, since the illumination lights R and B are irradiated from the different directions, a part in which only one of the reflected lights of the illumination lights is detected is generated according to the asperity. Accordingly, by detecting the reflected light "b" or "r" which is not mixed color, it is possible to detect only the asperity without detecting color-figure.

Figure 12:
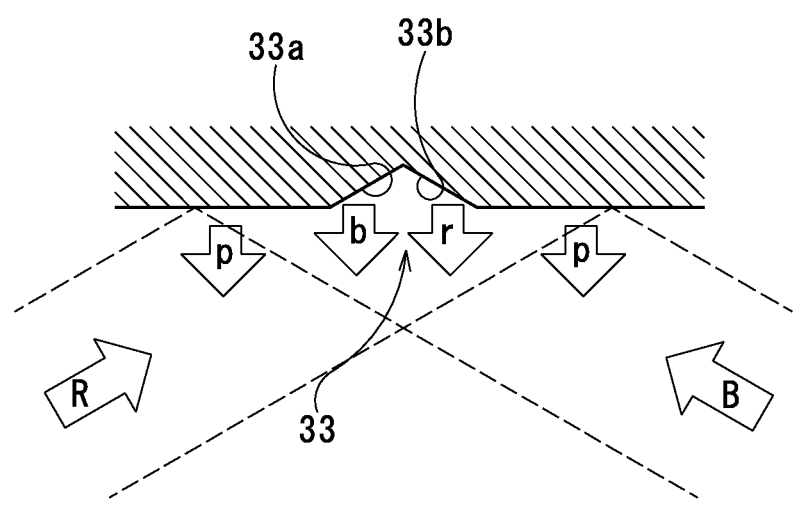
FIG. 12 It is a schematic view showing a reflection state of illumination lights having two colors at asperity in the inspection equipment shown in FIG. 1.
Figure 12:
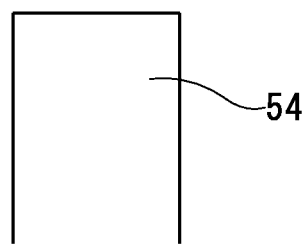

As shown in FIG. 12, if the dimple 33 is formed on the curl portion 32, the first-illumination light R is not irradiated to a non-reflection part 33a on the inner surface of the dimple 33. Accordingly, the red reflected light "r" of the first-illumination light R enters the second-imaging device 54 with making a shade of the non-reflection part 33a. On the other hand, the second-illumination light B irradiated from the different direction from the first-illumination light R is not irradiated to a non-reflection part 33b on the inner surface of the dimple 33. Accordingly, the blue reflected light "b" of the second-illumination light B enters the second-imaging device 54 with making a shade of the non-reflection part 33b. That is to say, the blue reflected light "b" from the non-reflection part 33a and the red reflected light "r" from the non-reflection part 33b enter the second-imaging device 54.

By irradiating the first-illumination light R and the second-illumination light B at the same time, as shown in FIG. 12, from the flat part without the asperity in the curl portion 32, the reflected light "p" having the mixed color is detected. On the other hand, from the inner surface of the dimple 33, the red reflected light "r" and the blue reflected light "b" are detected. Accordingly, at a part in which the reflected light "b" or "r" having single color according to the illumination lights B and R is detected, it is considered that asperity such as the dimple 33 is generated. Particularly, the reflected light "r" or "b" having single color is clearly detected because the first-illumination light R and the second-illumination light B are complementary colors to each other, the asperity can be reliably detected.

As explained above, according to the inspection equipment of the present invention, while inspecting fast in the first-inspection process by the white light, by eliminating all the bottle-cans in which the low-brightness area is detected in spite of whether or not the asperity is formed and then inspecting only those bottle-cans strictly in the second-inspecting process by the color inspection-image, so that the bottle-can having the asperity such as a flaw or the like can be reliably eliminated, and the processing time of inspection can be shortened.

The present invention is not limited to the above-described embodiments and various modifications may be made without departing from the scope of the present invention.

For example, in the inspection equipment of the above embodiment, each of the main-conveyance path and the second-conveyance path has one path. However, a plurality of paths may be provided in parallel for each. By providing the paths in parallel, a plurality of bottle-cans can be inspected at the same time, the processing time of inspection can be further shortened.

Figure 13:
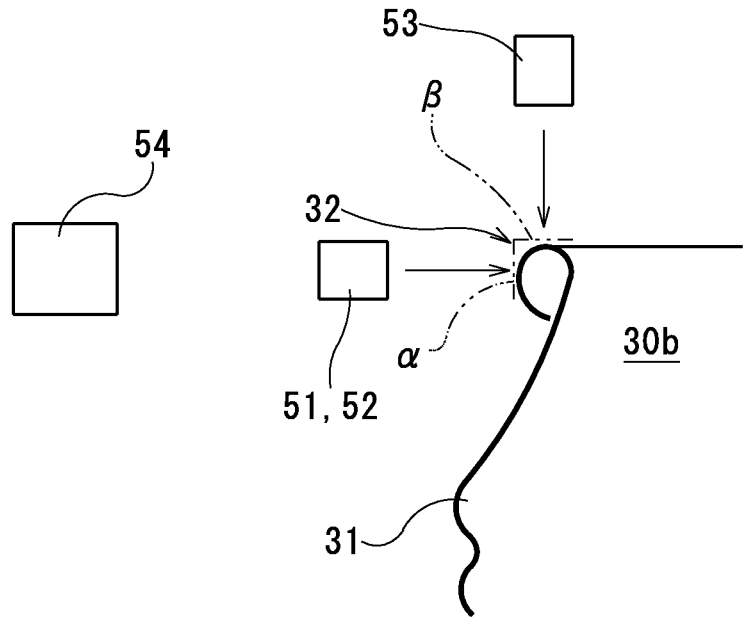
FIG. 13 It is a cross-sectional view showing an example in which an imaging area is set at an outer circumferential surface of a curl portion in inspection equipment for mouth section according to the present invention.

In the inspection equipment of the above embodiment, the imaging area to which the first-illumination light and the second-illumination light are irradiated is set on the top surface of the curl portion, and the third-illumination light is set so as to be irradiated to the outer circumferential surface of the curl portion. However, on the contrary to this embodiment, as shown in FIG. 13, the imaging area α may be set on the outer circumferential surface of the curl portion 32 and the edge-detection area β may be set on the top surface of the curl portion 32. In this case, the asperity formed on the outer circumferential surface of the curl portion 32 can be detected with distinguishing from the color-figure or the like, and it is possible to detect a defect such as a deformation in which a height of the top surface of the curl portion 32 varies.

In the inspection equipment of the above embodiment, one pair of the first-illumination device and the second-illumination device is provided, so that the first-illumination light and the second-illumination light are irradiated from the outer circumferential side the mouth section to the top surface of the curl portion. However, more than one set of the first-illumination device and the second-illumination device may be provided. For example, in a case in which the top surface of the curl portion is convexly bent, the illumination-lights are prevented by a protruded surface, so that the inner circumferential side of the top surface of the curl portion cannot be illuminated. Therefore, even though the asperity on the outer circumferential side of the top surface of the curl portion can be detected, it is difficult to detect the asperity on the inner circumferential side.

Figure 14:
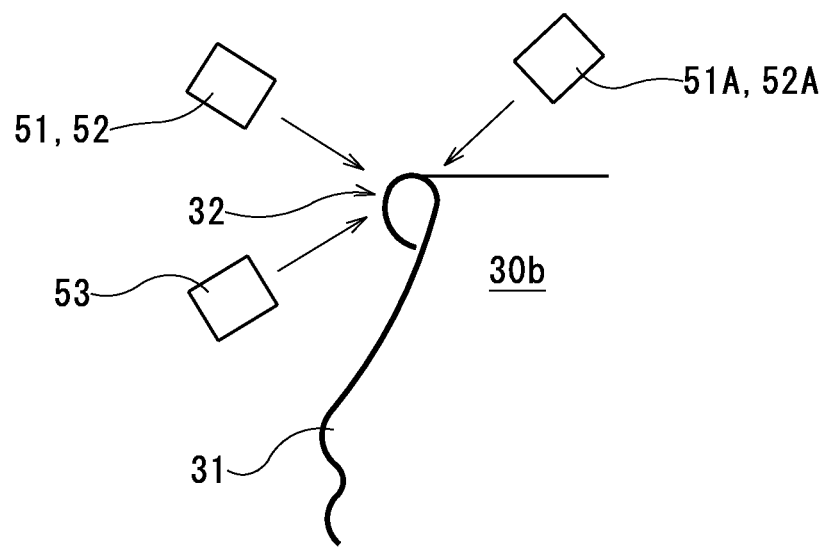
FIG. 14 It is a cross-sectional view showing an example in which two pairs of a first-illumination device and a second-illumination device are provided in inspection equipment for mouth section according to the present invention.
Figure 15:
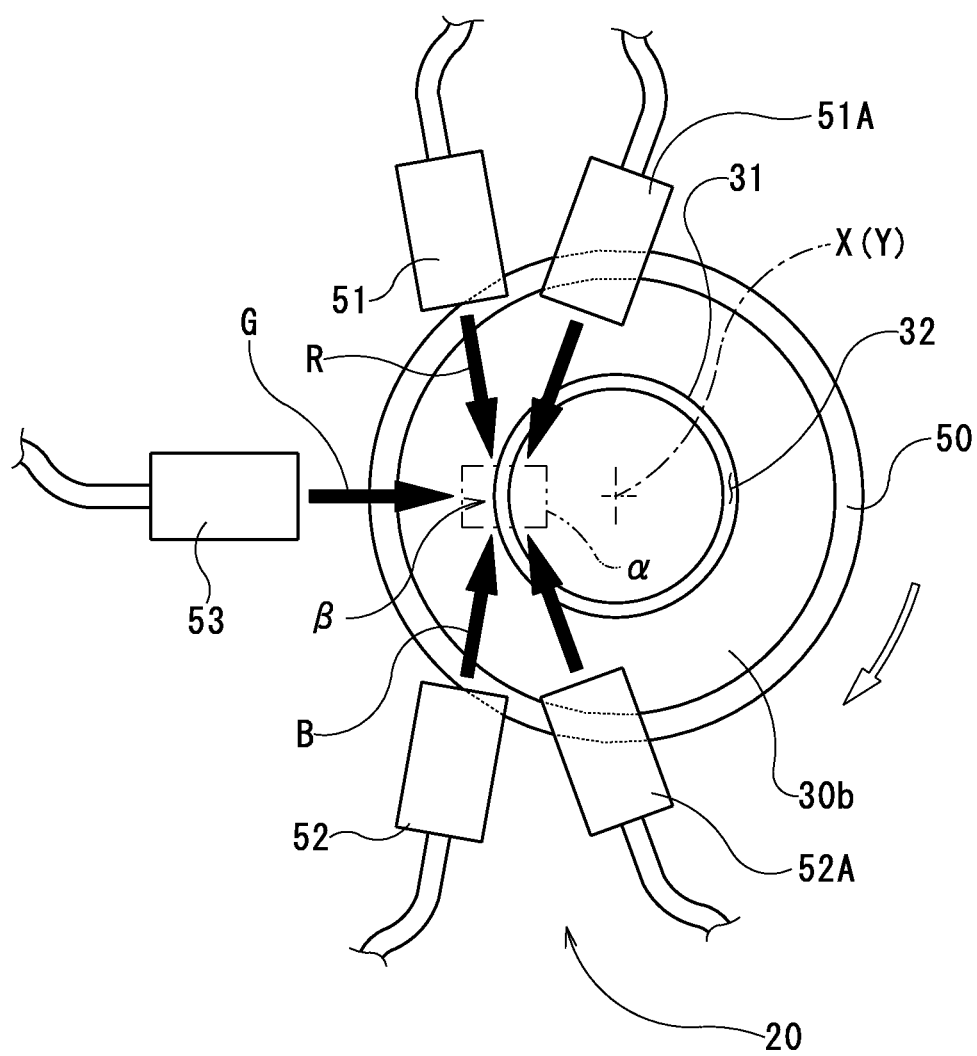
FIG. 15 It is a top view showing the inspection equipment shown in FIG. 14.

In this case, as shown in FIG. 14 and FIG. 15, in addition to the first-illumination device 51 and the second-illumination device 52 irradiating the illumination lights from the outer circumferential side of the mouth section 31 to the top surface of the curl portion 32, by providing a second pair of a first-illumination device 51A and a second-illumination device 52A irradiating illumination lights from the inner circumferential side of the mouth section 31 to the top surface of the curl portion 32, it is possible to inspect the top surface of the curl

INDUSTRIAL APPLICABILITY

An inspection method and inspection equipment the mouth section of bottle-can which can reliably detect only a bottle-can having asperity such as a flaw or the like which may cause liquid leakage or the like, and which can shorten the processing time for inspection with excellent productivity are provided.

DESCRIPTION OF THE REFERENCE SYMBOLS

100 inspection equipment for mouth section
10 first-inspection device
20 second-inspection device
30, 30a, 30b, 30c bottle-can
31 mouth section
32 curl portion
33 dimple
33a, 33b non-reflection part
34 pit
35 flaw
36 bent part
37 deformation
40 first-rotating device
41 white-light illumination device
42 first-imaging device
43 first-judging device
50 second-rotating device
51, 51A first-illumination device
52, 52A second-illumination device
53 third-illumination device
54 second-imaging device
55 second-judging device
R first-illumination light
B second-illumination light
G third-illumination light
r red reflected light
b blue reflected light
g green reflected light
p purple reflected light
X can-axis
Y rotating axis
α imaging area
β edge-detection area
E edge position
T top surface

The invention claimed is:

1. An inspection method for a mouth section of a bottle-can, with respect to the bottle-can having the cylindrical mouth section in which a curl portion is formed by curling an open end thereof for a cap with a liner to be put on, by taking an image of an imaging area which is set to include a part of the curl portion for detecting asperity at the curl portion while rotating the bottle-can around a can-axis, the inspection method comprising steps of:
    a first-inspection process for eliminating the bottle-can in which existence of a low-brightness area is detected from a monochrome inspection-image which is obtained by imaging the curl portion with irradiating white light to the curl portion in an imaging area of the bottle-can which is conveyed along a main-conveyance path continuously and sequentially; and
    a second-inspection process for judging quality of the bottle-can while conveying the bottle-can which is eliminated by the first-inspection process along a secondary-conveyance path deviated from the main-conveyance path, by irradiating illumination lights having two colors from different directions to the curl portion in the imaging area along substantially a tangential direction of a cylindrical surface of the mouth section so as to image a color inspection-image, and distinguishing existence or not of the asperity on the curl portion from signal strengths of the light colors of the color inspection-image.

2. The inspection method for mouth section of bottle-can according to claim 1, wherein in the second-inspection process, third illumination light having a light color different from that of the illumination lights having two colors is irradiated to a part to which the illumination lights having two colors are irradiated at the curl portion from a cross direction to the illumination lights having two colors.

3. Inspection equipment for a mouth section of a bottle-can, with respect to the bottle-can having the cylindrical mouth section in which a curl portion is formed by curling an open end thereof for a cap with a liner to be put on, by taking an image of an imaging area which is set to include a part of the curl portion for detecting asperity at the curl portion while rotating the bottle-can around a can-axis, the inspection equipment comprising:
   a main-conveyance path which conveys a bottle-can sequentially;
   a first-inspection device which eliminates the bottle-can in which existence of a low-brightness area is detected from a monochrome inspection-image which is obtained by imaging the curl portion with irradiating white light to the curl portion in an imaging area of the bottle-can which is conveyed along the main-conveyance path continuously and sequentially;
   a secondary-conveyance path which conveys the bottle-can which is eliminated by the first-inspection device; and
   a second-inspection device which judges quality of the bottle-can while conveying the bottle-can along a secondary-conveyance path, by irradiating illumination lights having two colors from different directions to the curl portion in the imaging area so as to image a color inspection-image, and distinguishing existence or not of the asperity on the curl portion from signal strengths of the light colors of the color inspection-image.

4. The inspection equipment for mouth section of bottle-can according to claim 3, wherein the first-inspection device comprises:
   a first-rotating device which holds the bottle-can and rotates the bottle-can around the can-axis;
   a white-light illumination device which irradiates white light to the curl portion in the imaging area;
   a first-imaging device which images the imaging area in monochrome; and
   a first-judging device which eliminates the bottle-can based on a detection result of detecting the low-brightness area from the monochrome inspection-image obtained by the first-imaging device,
and the second-inspection device comprises:
   a second-rotating device which holds the bottle-can which is eliminated by the first-inspection device and rotates the bottle-can around the can-axis;
   a first-illumination device which irradiates a first-illumination light to the curl portion in the imaging area of the bottle-can along substantially a tangential direction of a cylindrical surface of the mouth section;
   a second-illumination device which irradiates a second-illumination light having a light color different from that of the first-illumination device to a part to which the first-illumination light is irradiated at the curl portion from an opposite side of the first-illumination light with the imaging area in between along substantially the tangential direction of the mouth section;
   a second-imaging device which images the imaging area in color; and
   a second-judging device which judges quality of the bottle-can by distinguishing the existence or not of the asperity from the signal strengths of the light colors of the color inspection-image obtained by the second-imaging device.

5. The inspection equipment for mouth section of bottle-can according to claim 3, wherein the second-inspection device further comprises a third-illumination device which irradiates third illumination light having a light color different from that of the illumination lights having two colors to a part to which the illumination lights having two colors are irradiated at the curl portion from a cross direction to the illumination lights having two colors.

6. The inspection equipment for mouth section of bottle-can according to claim 4, wherein the second-inspection device further comprises a third-illumination device which irradiates third illumination light having a light color different from that of the illumination lights having two colors to a part to which the illumination lights having two colors are irradiated at the curl portion from a cross direction to the illumination lights having two colors.

* * * * *